US00PP08622P

United States Patent [19]

Lopez

[11] Patent Number: Plant 8,622

[45] Date of Patent: Mar. 1, 1994

[54] STRAWBERRY PLANT NAMED CARTRES

[75] Inventor: Jose M. A. Lopez, Tudela - Navarra, Spain

[73] Assignee: Plantas de Navarra, S.A., Valtierra, Spain

[21] Appl. No.: 901,502

[22] Filed: Jun. 19, 1992

[51] Int. Cl.[5] ..... A01H 5/00

[52] U.S. Cl. ..... Plt./49

[58] Field of Search ..... Plt. 48, 49

*Primary Examiner*—James R. Feyrer
*Assistant Examiner*—E. F. McElwain
*Attorney, Agent, or Firm*—Christie, Parker & Hale

[57] ABSTRACT

A strawberry plant producing substantially conical fruit of bright color.

3 Drawing Sheets

BACKGROUND OF THE INVENTION

The new variety of strawberry was created in a breeding program by my crossing two parents from among a group of seedlings which were obtained from a free pollenization of 32 different varieties and seedlings; in particular, by crossing as seed parent a variety designated 86-175 and as pollen parent a variety designated 86-189. Both parental varieties are proprietary and have not been commercialized.

The resulting seedling of the new variety was grown and asexually propagated by stolens in Soria, Spain. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Cartres'. Among the characteristics which distinguish the new variety from other varities of which I am aware are a combination of traits which include inflorescence at about the same level as the foliage, long, approximately conically shaped bright red fruit.

COMPARISON TO CLOSEST VARIETY

The variety which I believe to be closest to 'Cartres' from those known to me is the variety 'Chandler'. The characteristics of the new variety that are different from, or not possessed by, 'Chandler' include: darker green coloration where leaves bunch, a stronger blistering of the leaf and occasional number of folioles greater than three. In the petiole the position of the hairs is upwards. In fruit the achenes are below the surface. The shape of the teeth of the terminal leaflet are obtuse. The flowers of the new variety tend to be at the same level of the foliage and the fruit are more conical. 'Chandler' is the subject of U.S. Plant Pat. No. 5,262, which may be referred to for further information on this variety.

BRIEF DESCRIPTION OF THE ILLUSTRATIONS

The accompanying photographs show typical specimens of the new variety, including fruit, foliage and flower, in color as nearly true as it is reasonably possible to make in color illustrations of this character.

Two illustrations show typical fruit in cross section illustrating the typical flesh and flesh coloration, conspicuous core and near conical shape (note that the designation "89-62-022" refers to the new variety);

Another illustration shows the fruit and foliage;

A fourth illustration shows the flower and reproductive organs of the new variety; and A fifth illustration shows the top and undersurface of a typical foliole of the new variety.

DESCRIPTION OF THE NEW VARIETY

The following detailed description of the new variety is based upon observations taken of plants and fruit grown "underglass", i.e., undertunnel, in the farm of La Mogalla in Cartaya (Huelva), Spain. This description is in accordance with UPOV terminology and the color terminology herein is in accordance with The Royal Horticultural Society Colour Chart (R.H.S.C.C.) and the color descriptions refer to plate numbers in the aforementioned color chart. Color designations, color descriptions and other phenotypical descriptions may deviate from the stated values and descriptions depending upon variation in environmental, seasonal, climatic and cultural conditions.

Propagation

The new variety is principally propagated by way of stolens. Although propagation by stolens is presently preferred, other known methods of propagating strawberry plants may be employed. It has been determined that the plants root well after transplanting.

The following additional information is provided to further describe the new variety.

Plant:

*Habit.*—Globose.
*Density.*—Medium.
*Vigor.*—Medium.
*Height.*—About 16 cm.
*Width.*—About 26 cm.

Foliage:

*Leaf.*—Color: Upper side — near 139A. Underside — near 139C to 139D. Cross Section: Slightly concave. Blistering: Strong texture or rugosity. Number of leaflets: Sometimes more than three. Length: About 10 cm. Width: About 11 cm.

*Terminal leaflet (length to width ratio).*— Longer than broad; Length — About 7 cm, Width — About 6 cm.

*Terminal leaflet (shape of base).*— Rounded.

*Terminal leaflet (shape of teeth).*— Obtuse.

*Petiole.*—Pose of hairs: Upwards; Length of petiole — about 10 cm.

*Stipules.*—Anthocyanin coloration: Medium.

*Stolens.*—Number: Medium. Anthocyanin coloration: Weak (light). Thickness: Medium. Pubescence: Weak.

Flower:

*Size.*—Large; Primary flower — About 4 cm, Secondary flower — About 3 cm.

*Size of calyx relative to corolla.*—Larger.

*Size of inner calyx relative to outer.*—Same size.

*Spacing of petals.*—Overlapping.

*Petal length to width ratio.*—Broader than long.

*Petal color.*—White.

*Separation of the petals of flowers with* 5 or 6 petals-.—Overlapping each other.

*Fruiting truss..*—Attitude (at first picking): Semi-erect.

*Inflorescence.*—Level with foliage.

Fruit:

*Ratio of length to maximum width.*—Much longer than broad

*Size.*—Large; Primary fruit — length about 6.5 cm, width about 3.5 cm; Secondary fruit — Length about 5 cm, width about 3 cm.

*Predominant shape.*—conical.

*Difference in shapes between primary and secondary fruits.*—Slight.

*Band without achenes.*—Absent or very narrow.

*Unevenness of surface.*—Medium.

*Color.*—Red, near 44B.

*Evenness of color.*—Even.

*Glossiness.*—Strong.

*Insertion of achenes.*—Below surface.

*Insertion of calyx.*—Level.

*Pose of the calyx segments.*—Reflexed.

*Size of calyx in relation to fruit diameter.*—Same size.

*Adherence of calyx.*—Medium.

*Firmness.*—Very firm.

*Color of flesh.*—Near 42B to 42C, medium red.

*Evenness of color of the flesh.*—Even.

*Sweetness.*—Medium.

*Acidity.*—Weak.

*Time of flowering* (50% *of plants at first flower*)-.—Medium.

*Time of ripening* (50% *of plants with ripe fruits*)-.—Medium.

*Type of bearing.*—Not remontant.

*Fruiting (La Mogalla, Spain).*—For plants planted October 21, about 10% flowering occurs about December 8, first mature fruit about January 27, maturity (15-20 gm/plant) about Feb. 9.

I claim:

1. A new and distinct variety of strawberry, substantially as shown and described.

* * * * *

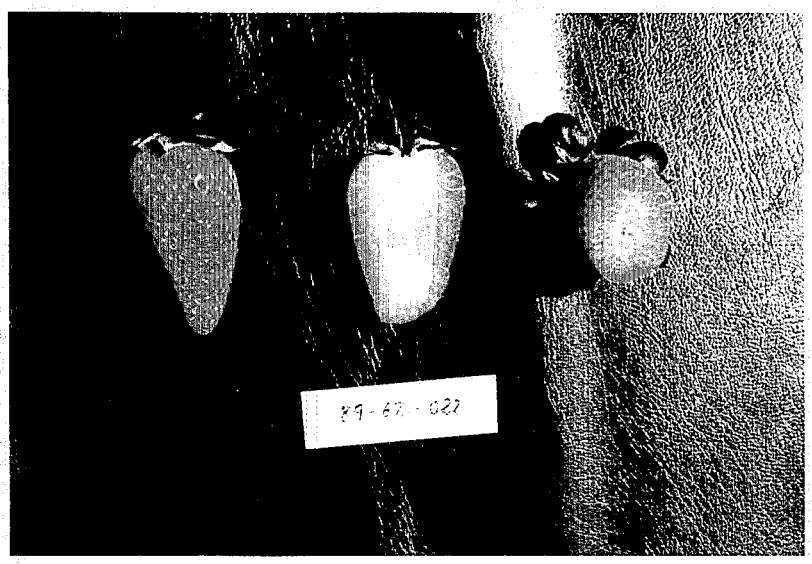
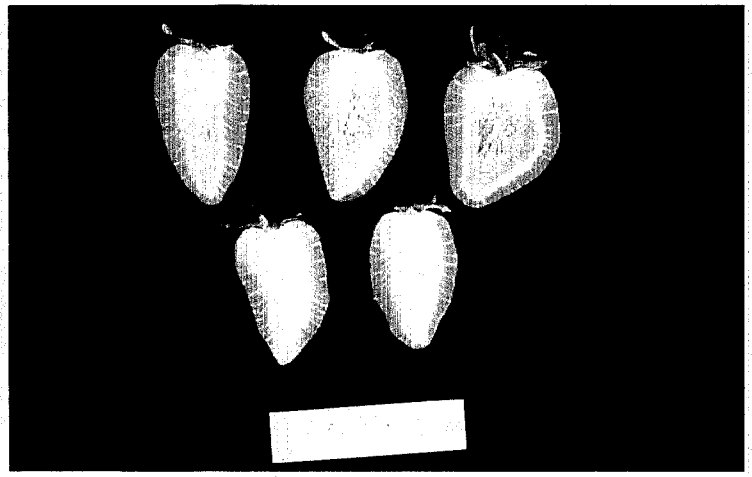

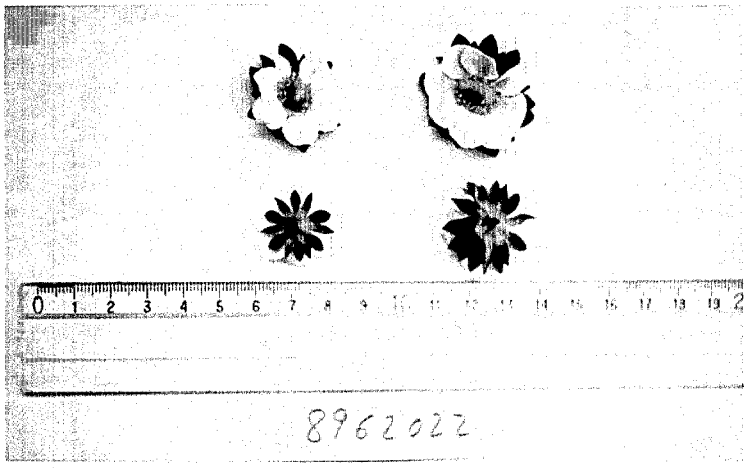
8962022
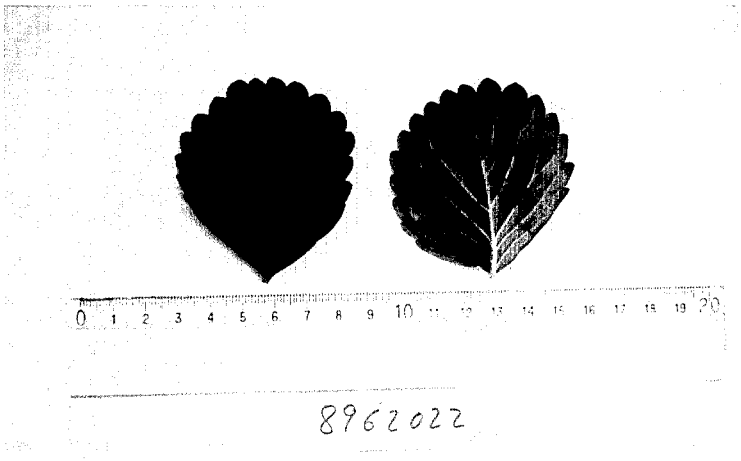
8962022

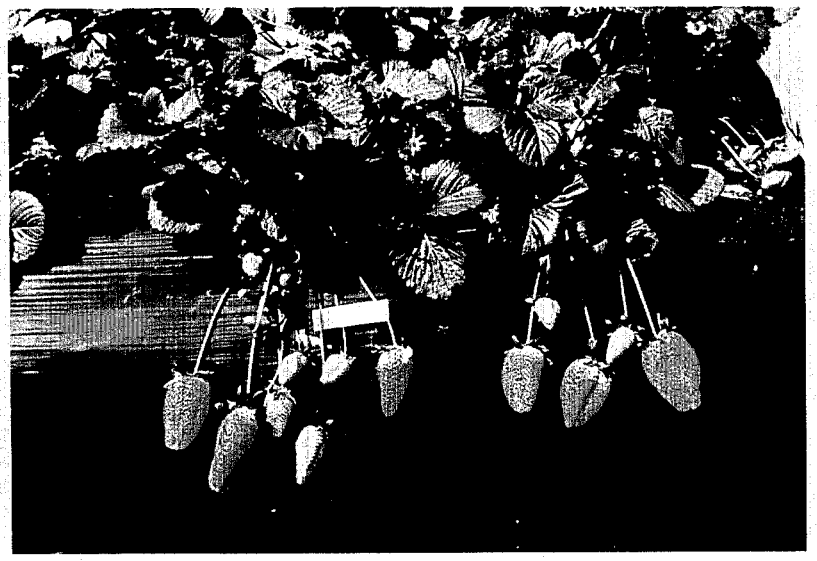

UNITED STATES PATENT AND TRADEMARK OFFICE

CERTIFICATE OF CORRECTION

PATENT NO. : Plant 8,622

DATED : March 1, 1994

INVENTOR(S) : Jose M.A. Lopez

It is certified that error appears in the above-indentified patent and that said Letters Patent is hereby corrected as shown below:

On the Cover Page:

References Cited, U.S. PATENT DOCUMENTS, column 2, before "[58]" insert the following:

-- [56] Reference Cited
U.S. PATENT DOCUMENT
P.P. 5,262 7/1984 Voth et al...Plt.48 --.

Column 1, line 25, change "varities" to -- varieties --.

Signed and Sealed this

First Day of November, 1994

Bruce Lehman

*Attest:*

BRUCE LEHMAN

*Attesting Officer*

*Commissioner of Patents and Trademarks*